(12) United States Patent
Pelletier et al.

(10) Patent No.: US 7,330,034 B1
(45) Date of Patent: Feb. 12, 2008

(54) MOISTURE MEASUREMENT SYSTEM FOR SEED COTTON OR LINT

(75) Inventors: Mathew G. Pelletier, Lubbock, TX (US); Michael E. Gvili, Wayland, MA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 419 days.

(21) Appl. No.: 11/011,705

(22) Filed: Dec. 14, 2004

Related U.S. Application Data

(60) Provisional application No. 60/533,843, filed on Dec. 31, 2003.

(51) Int. Cl.
*G01R 27/04* (2006.01)
(52) U.S. Cl. ...................... 324/640; 324/634
(58) Field of Classification Search ................ 324/640, 324/634
See application file for complete search history.

(56) References Cited

U.S. PATENT DOCUMENTS

| | | | |
|---|---|---|---|
| 4,361,801 A | 11/1982 | Meyer et al. | |
| 5,333,493 A | 8/1994 | Cutmore | |
| 6,107,809 A * | 8/2000 | Moshe et al. | 324/640 |
| 6,111,415 A | 8/2000 | Moshe | |
| 6,147,503 A | 11/2000 | Nelson et al. | |
| 6,476,619 B1 | 11/2002 | Moshe et al. | |
| 6,691,563 B1 * | 2/2004 | Trabelsi et al. | 73/73 |
| 2006/0028213 A1 * | 2/2006 | Typpo et al. | 324/640 |

* cited by examiner

*Primary Examiner*—Vincent Q. Nguyen
(74) *Attorney, Agent, or Firm*—John D. Fado; Randall E. Deck; Lesley Shaw

(57) ABSTRACT

A process for measuring the moisture content and the mass-moisture content of materials is presented that requires no air reference or calibration sequence. A microwave signal is split into a reference and a transmission signal, and the reference signal is applied directly to the phase detector, whereas the transmission signal is first transmitted through the sample before being presented to the other side of the phase detector. This measurement provides a phase-constant measurement that is due to the dielectric characteristics of the material under test. The system measures the material's phase-constant across a band of frequencies. The slope of the phase-constant versus frequency is then utilized to predict the density of the material which is then combined with the corrected phase-constant measurement to calculate the moisture content of the material.

11 Claims, 6 Drawing Sheets

Figure 1) This illustration depicts the high correlation between the derivative of the phase measurement and the bulk density independently of moisture.
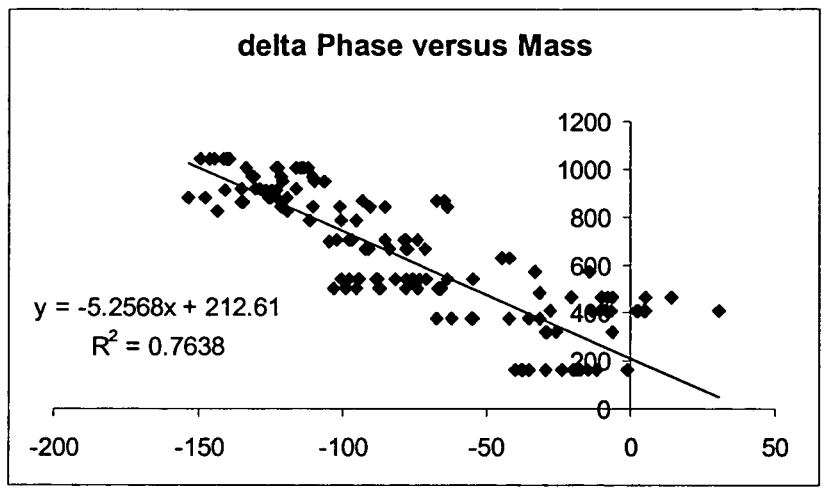
Figure 2) This figure illustrates the very poor correlation between a delta phase measurment to moisture.
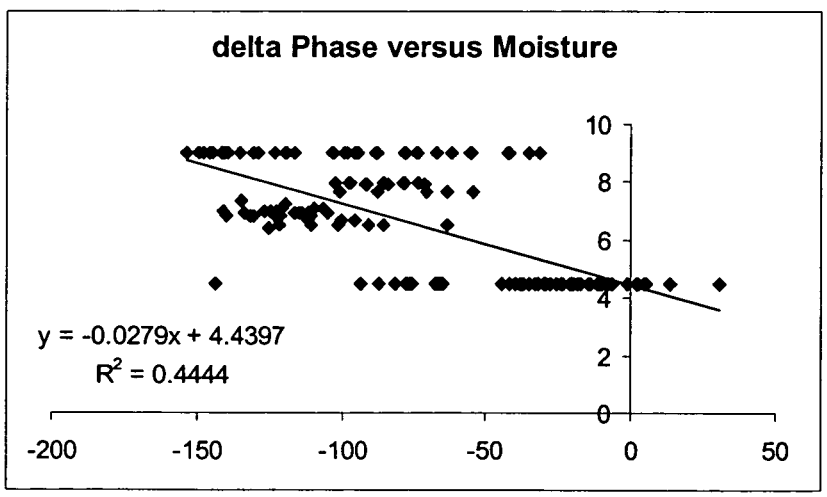

figure 3) This shows the improved relationship of the delta phase measurement to the moisture density (mass*moisture).
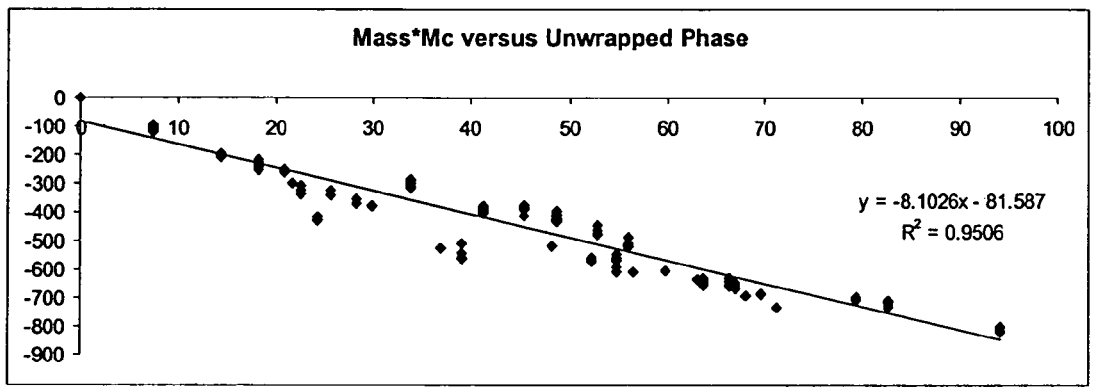
Figure 4) The log of the dielectric constant of water versus the log of the frequency from DC to $10^{16}$ Hz.
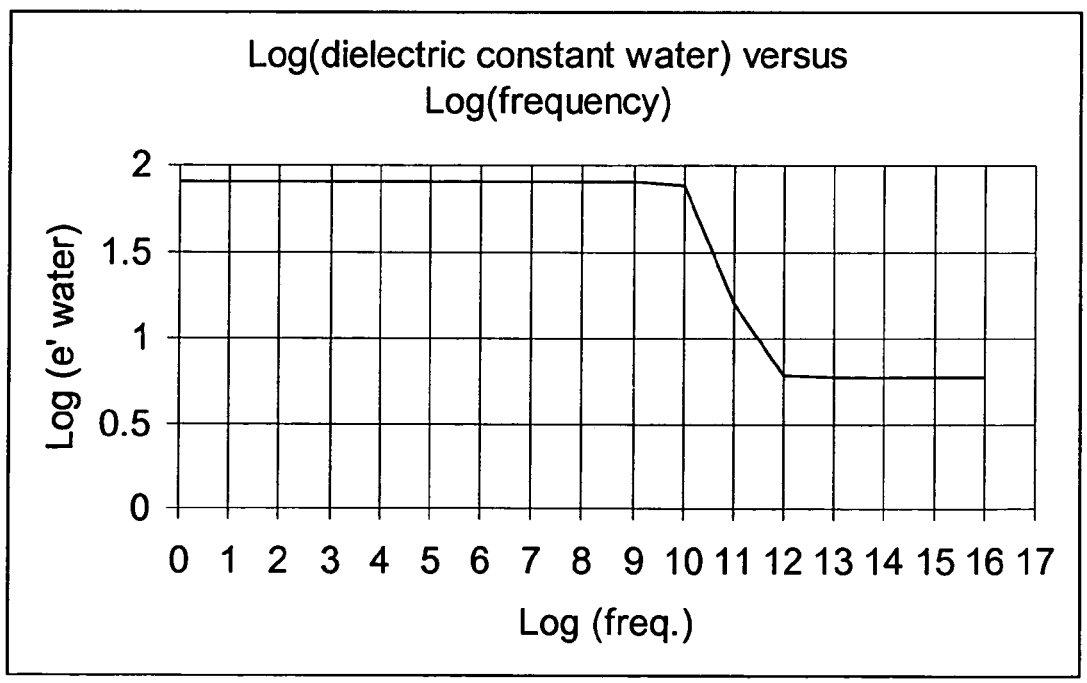

Figure 5) The Von Hippel data set for the dielectric of water at 25 degrees C as published in Dielectric Materials and Applications. 1954 MIT Press.
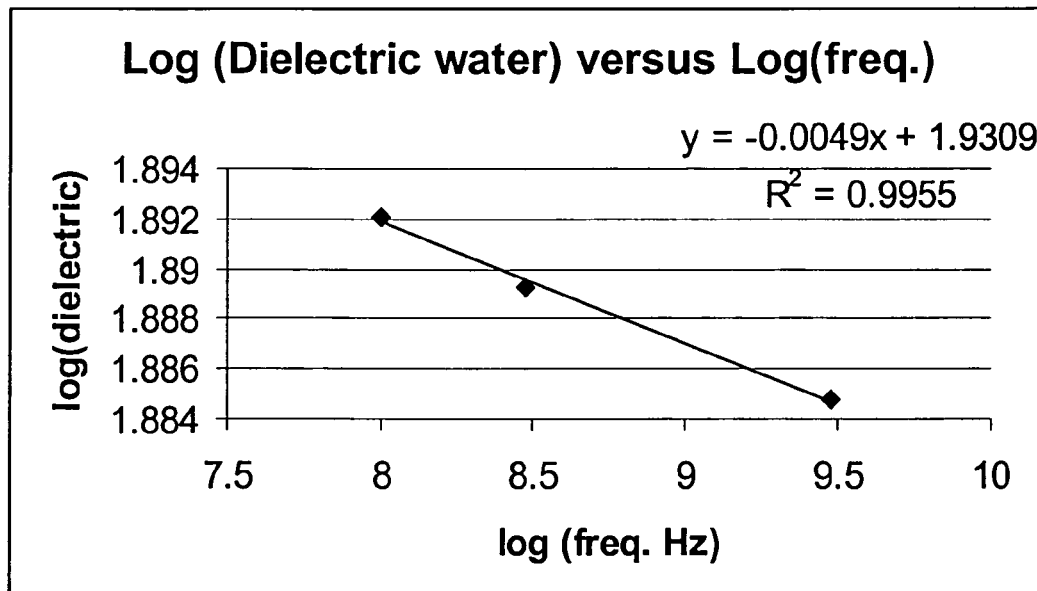
Figure 6: Moisture content determination of cotton bales utilizing the measurement of the phase constant technique in conjunction with a weight determination method.
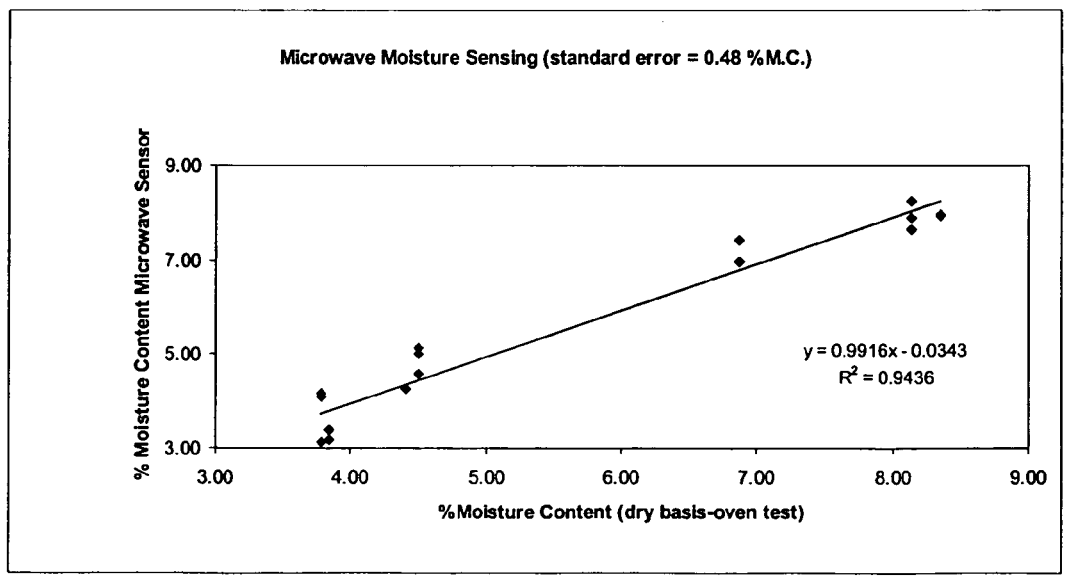

Figure 7. Frequency Synthesizer Diagram
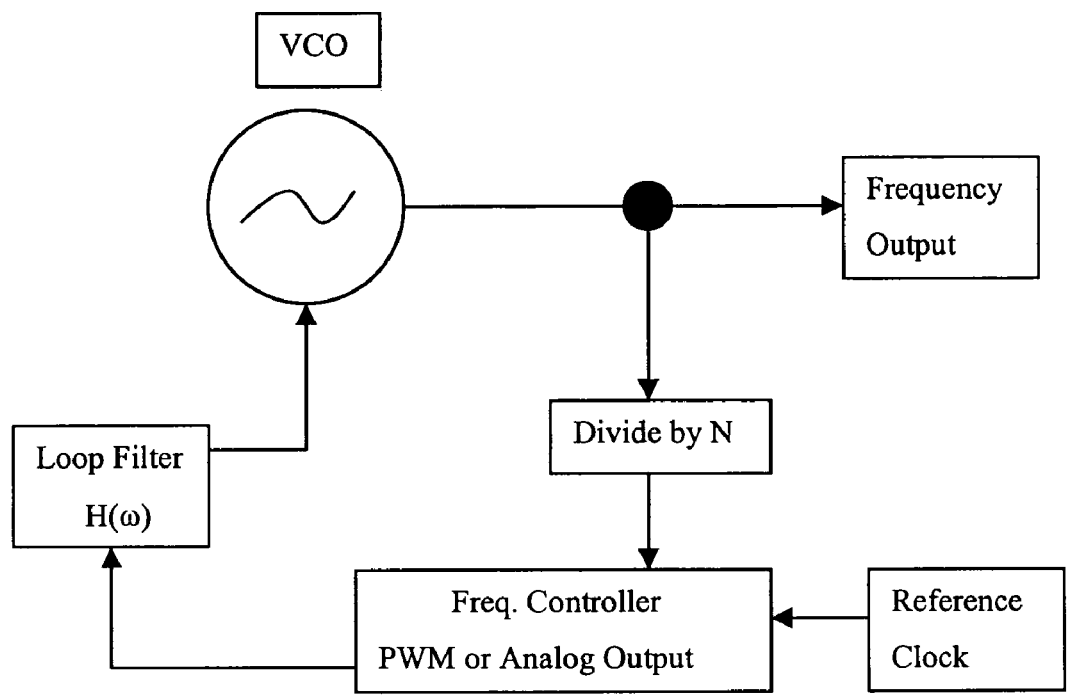

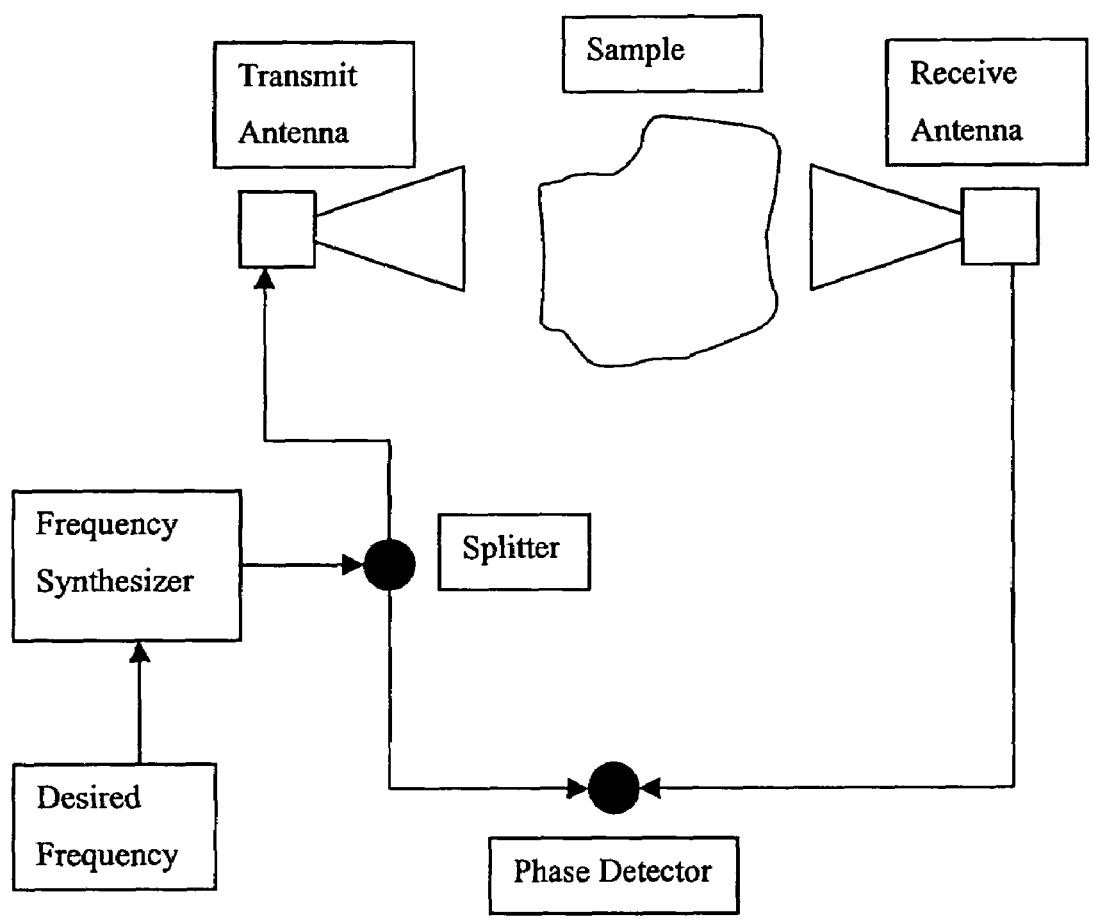
Figure 8. System Diagram

MOISTURE MEASUREMENT SYSTEM FOR SEED COTTON OR LINT

BACKGROUND OF THE INVENTION

1. Field of the Invention

This invention relates to a moisture sensor system for cotton. More specifically, a system of microwave moisture sensing is disclosed for the measurement of moisture in lint and/or seed cotton being processed in a cotton gin. The system provides the ability to quantify the amount of water in seed cotton/lint.

2. Description of the Prior Art

Modern cotton gins have the purpose of extracting lint (the cotton) from trash and seeds—usually the sticks, leaves and burrs that are entrained with the cotton. These modern gins include many individual machine components that are operated sequentially to form the gin processing line. The components are often specific in the types of trash that they remove. Stick machines, inclined cleaners, and especially lint cleaners process the lint to a purity where it can be baled and delivered to spinning mills. Included in these systems are drying systems as it is imperative that the cotton must be within a range of moisture contents in order for the machinery to work properly.

Unfortunately, the cotton processed by such machines varies widely in moisture content and to date the technology available to measure the moisture content is limited to inaccurate low cost resistance moisture sensors or extremely expensive microwave moisture sensors. Thus, only a very few cotton gins are even attempting to measure the moisture content even though control over the moisture content is critical to the operation of the cotton gin in terms of both productivity as well as for the preservation of the required quality standard for the ultimately produced lint cotton.

This need to produce a better quality product for sale to the cotton textile mills and to reduce labor costs during processing has led to considerable interest in process control for cotton gins. Anthony and Byler (1994) indicate that process control can range from $15,000 to $100,000. Most of the work to date has involved the online measurement of moisture and trash. It is inevitable that the cotton gins in the near future will become fully computerized and automated (Byler and Anthony, 1997). This is due to the fact that optimal control of the gin will produce optimal economic returns for a given ginned bale of cotton. This will be advantageous to the growers, the ginners, and the processing mills as they will receive a consistent product that can be tailored to their desired specifications. In this regard, it is expected that the gins will become fully automated in the near future as suitable low cost technology becomes available. It has already been shown that this automation will utilize some form of moisture measurement system at several key locations scattered throughout the ginning process.

Byler and Anthony (1997) reported on a computer-based cotton color and trash and moisture measurement system that was used to control the drying and cleaning machinery. This system utilizes a resistance sensor. The system can only be made to work when used in conjunction with a sampling system that presents a solid piece of lint (no voids or holes) and at a uniform packing density to remove the effect of varying lint density from the measurement. This system was installed at a gin in Cortland, Ala. in 1994. In 1994, it was reported to be the most complete computerized gin process control system in the world. This process control system utilized two trash and moisture level sensors. The cotton moisture/color/trash sensors were based upon the High-Volume-Instruments (HVI) that are used in the United States Department of Agriculture's Cotton Classing Office. The first sensor was located opposite of a ram located in the back of the feed control. The feed control is located before the gin stand where the lint is removed from the seed cotton. The ram was periodically extended to press cotton against a glass sample imaging and resistance sensing plate. The second color/trash/moisture measurement station was located after the gin stand and before the lint cleaners. A paddle sampler was used to obtain a sample from the duct and press the sample against a sensing window.

Byler (1992) reported that sample compression against a resistance sensing plate was used to increase the sample density in order to produce a more repeatable moisture reading by minimizing the sample density variations. The sample compression was felt to be important enough that several devices were developed to accomplish this and U.S. Pat. No. 5,125,279 Jun. 30, 1992 entitled System for Analyzing Cotton was obtained for a paddle sampler to accomplish the sample extraction compression for the trash, moisture and color measurement, as well as the moisture sensing U.S. Pat. No. 5,514,973 which is based upon resistance sensing. It is still in use to date in the Zellweger Uster Intelligin and was reported to be fully functional in two commercial gin's as conducted in a USDA study (Anthony et al., 1995).

Another disadvantage to this technique is the need for pressing the cotton against a resistance sensing plate, as this restricts the possible locations where this technique can be applied in a cotton gin in addition to the very likely possibility of stoppage/blockage of the cotton flow due to system malfunctions.

The final stage in the cotton processing stream is the cotton bale packaging system. Recent innovations has shown that the use of cotton moisture restoration systems both reduce stress on the pale packaging system as well as add additional weight to the bales. As cotton is sold on a wet basis there is a real market incentive for the utilization of these systems. As such, currently there are no resistive sensors that can be accurately used to control these systems as the surface moisture these systems add to the cotton alter the calibration of these sensors in an uncontrolled manner. The only other types of sensors that can be utilized are very expensive microwave bale moisture sensors that are typically utilizing very high frequency microwave technology that is prohibitively expensive to manufacture. Given this fact there are a large number of cotton gins that are using moisture restoration systems without any type of feed back control sensor to maintain the correct moisture in the cotton bales.

Cotton bales are provided an official grade that is based upon samples obtained immediately upon the baling of the cotton. These samples are shipped to a USDA-AMS classing office where both the color and trash content are measured. This grade is then used to set the value of that particular bale of cotton. Unfortunately, when moisture is added to the bale in an excessive amount, this grade has been shown to change as the moisture degrades the cotton. This has led to hundreds of bales being returned back to the gins and has caused a great deal of concern in the industry over the potential damage to the USDA-AMS classing grade. Given this situation it is critical that a low cost moisture measurement system is developed that will determine the moisture content of the cotton bales. This system could then be easily deployed at an affordable price to all gins that are using moisture restoration and will protect and maximize the quality and value of their cotton as well as preserve and protect the reputation of US cotton and USDA-AMS cotton grades.

In the field of non-contact moisture sensing, there exists two main styles of radio frequency sensing systems, near and far field detection. An example of a near field system which is based upon a very low frequency rf field measurement, U.S. Pat. No. 6,275,046. This system utilizes a near-field electric field measurement which to date has demonstrated poor repeatability, low accuracy and severe drift over time problems. Other more relevant instruments of note are of several microwave sensor patents.

U.S. Pat. No. 2,659,860 teaches a method to measure the moisture content of bales of material, by directing a 10 GHz microwave beam through the bale and receiving the beam with another antenna on the far side of the bale from the one which generated the signal. The moisture content of the bale is then determined solely from the attenuation of this signal.

Meyer and Schilz U.S. Pat. No. 4,361,801 teaches a sensing technique that requires measurements of both attenuation and the phase delay of propagation in order to calculate the real and the imaginary components of the complex permittivity measurement in order to measure moisture at 9 GHz which is independent of density. The basis for this measurement is the ratio of the complex permittivities providing which is a modification of taking the ratio of the attenuation to the propagation delay as the measure of moisture (either as phase delay or equivalently the time delay). Nelson et al. U.S. Pat. No. 6,147,503 describes another moisture sensor algorithm that provides a moisture sensor that is independent of density over the narrow range of densities provided by loose seed kernel samples versus tightly packed seed kernel samples. They teach a technique that operates at 11.3 and 18 GHz again using the both the attenuation and the propagation delay to calculate the complex permittivity of the material to derive an algorithm for the determination of the moisture content of the material. Moshe et al. U.S. Pat. No. 6,476,619 describes a microwave cavity perturbation technique for the sensing of moisture and or density in cotton sliver that has a preferred operating range of 7-9 GHz. In the perturbation technique the system is setup with a resonant peak in the signal amplitude versus frequency plot and utilizes the frequency change in the location of this peak as the measure of permittivity change thereby providing a measure of the permittivity from which the moisture content can be estimated assuming a constant density of material. Patents by Moshe et al. include U.S. Pat. Nos. 5,845,529 and 6,107,809 in which they utilize a ratio of attenuation to phase delay measurement in a manner very similar to the Meyer and Schilz U.S. Pat. No. 4,361,801. The reoccurring theme between all of these patents is that they all use very high microwave frequencies, typically above 7 GHz, and all of them utilize a measure of the attenuation of the signal after it has been transmitted through the material under test as the primary measure of the moisture content. The only reference in the literature to the use of a phase only measurement for use in moisture sensing is from Cutmore, U.S. Pat. No. 5,333,493 that discusses the use of utilizing a raw relative phase delay measurement, at frequencies ranging from 2 GHz-10 GHz, in which the raw relative phase delay is the measured difference between the transmitting signal that has passed through the material and an internal reference of that signal that has not passed through the material. This uncalibrated and uncorrected relative phase delay is sampled over a small range of frequencies and the average of these uncorrected relative phase delays are then utilized as the measure of moisture of material along with a known density of the material. What is not appreciated in that invention is that any change in the system such as movement of any of the antennas, the addition of a neighboring metallic object, a different length coax cable, a new antenna etc. will all alter this raw relative phase delay in an unpredictable way, thereby forcing the operator of the system to have to recalibrate the system before it can become usable again. As this recalibration process is an expensive and time consuming task that is not addressed by this patent, it represents a serious issue in which a solution that avoids this issues would be preferred. As such it is one objective of this invention to provide a technique that will provide repeatable measurements irrespective of the antennas, antenna placements, coax length and such.

In the previously described prior art patents, all of these patents provide very expensive solutions as they all utilize frequencies well above 2 GHz. Additionally, it should be noted that the radar cross-section of the typical metal bale ties is very large at these high microwave frequencies and has been shown to cause significant signal interference at these very high frequencies, thereby rendering all of these frequencies unusable for use in moisture measurement of metal tied cotton bales.

SUMMARY OF THE INVENTION

We have now invented an improved process for measuring the moisture content of a test material. The process of the invention includes the steps of:

producing two or more stable primary microwave signals which have different frequencies with a frequency synthesizer, splitting each of the primary signals to provide a first and second microwave signal from each single primary signal, wherein the first signals are to be transmitted once through the material and once through air only in place of the material, and the second signals provide internal reference signals, transmitting the first signals through at least a portion of the test material, receiving at a receiver, the first signals which have passed through the material, transmitting the first signals through air only, receiving at a receiver the first signals which have passed through air only, measuring the phase difference between each second signal and each first signal which has passed through only air in place of the material, which signals are at the same frequency, and determining therefrom the air reference phase delay at those different frequencies, measuring the phase difference between each second signal and each first signal which has passed through the material, which signals are at the same frequency, and determining therefrom the material phase delay at those different frequencies, calculating the difference between the air reference phase delay and the material phase delay to determine the instrument corrected material phase delay at those different frequencies, obtaining the weight or density of the material, and calculating the moisture content of the material from the instrument corrected material phase delays and the obtained weight or density.

While the weight or density of the material may be obtained by conventional techniques, in a preferred embodiment they too are calculated from the delta phase measurement.

The calculation of the material's weight or density utilizes the same steps described above, of producing two or more primary microwave signals, splitting those signals, transmitting first signals through the material or air only, receiving those first signals, measuring the phase differences to determine the air reference phase delays and material phase delays, and calculating the difference between the air reference phase delay and the material phase delay to determine an instrument corrected material phase delay at the different frequencies. However, following the determination of the instrument corrected material phase delays at the different frequencies, the weight and density determination includes the steps of:

determining a delta phase measurement from the corrected material phase delay at the different frequencies, and calculating the weight or density of the material from the delta phase measurement.

In a preferred embodiment, the delta phase measurement is determined from the derivative of the instrument corrected material phase delays at the different frequencies. In a particularly preferred embodiment, this delta phase measurement is obtained by:

unwrapping the instrument corrected material phase delay to provide a continuous curve of instrument corrected phase delay versus frequency, and determining therefrom the unwrapped instrument corrected phase delay, and calculating the difference between the highest and lowest frequency's unwrapped instrument corrected phase delay, and determining therefrom the derivative of the unwrapped instrument corrected phase delay versus frequency to produce a delta phase measurement.

In accordance with this discovery, it is an object of this invention to provide an improved microwave process and system for measuring the moisture content of cotton bales and other materials.

Another object of this invention is to provide an improved microwave process and system for measuring the weight or density of cotton bales and other materials.

Other objects and advantages of the invention will become readily apparent from the ensuing description.

BRIEF DESCRIPTION OF THE DRAWINGS

FIG. 1 illustrates the high correlation between the derivative of the phase measurement to the bulk density.

FIG. 2 illustrates the poor correlation between the derivative of the phase measurement to moisture.

FIG. 3 illustrates the improved correlation between the derivative of the phase measurement to the moisture-density or mass times moisture.

FIG. 4 illustrates the stable dielectric constant of water for frequencies below 1 GHz.

FIG. 5 illustrates that the dielectric constant between 100 MHz and 3 GHz is a linear relation between log (freq) and the log (dielectric).

FIG. 6 illustrates the dielectric constant between 100 MHz and 3 GHz is a linear relation between log (freq) and the log (dielectric).

FIG. 7 is a block diagram of the frequency synthesizer.

FIG. 8 is a block diagram of a typical configuration of the hardware used in the moisture sensing system of this invention.

DETAILED DESCRIPTION OF THE INVENTION

Figure 9:
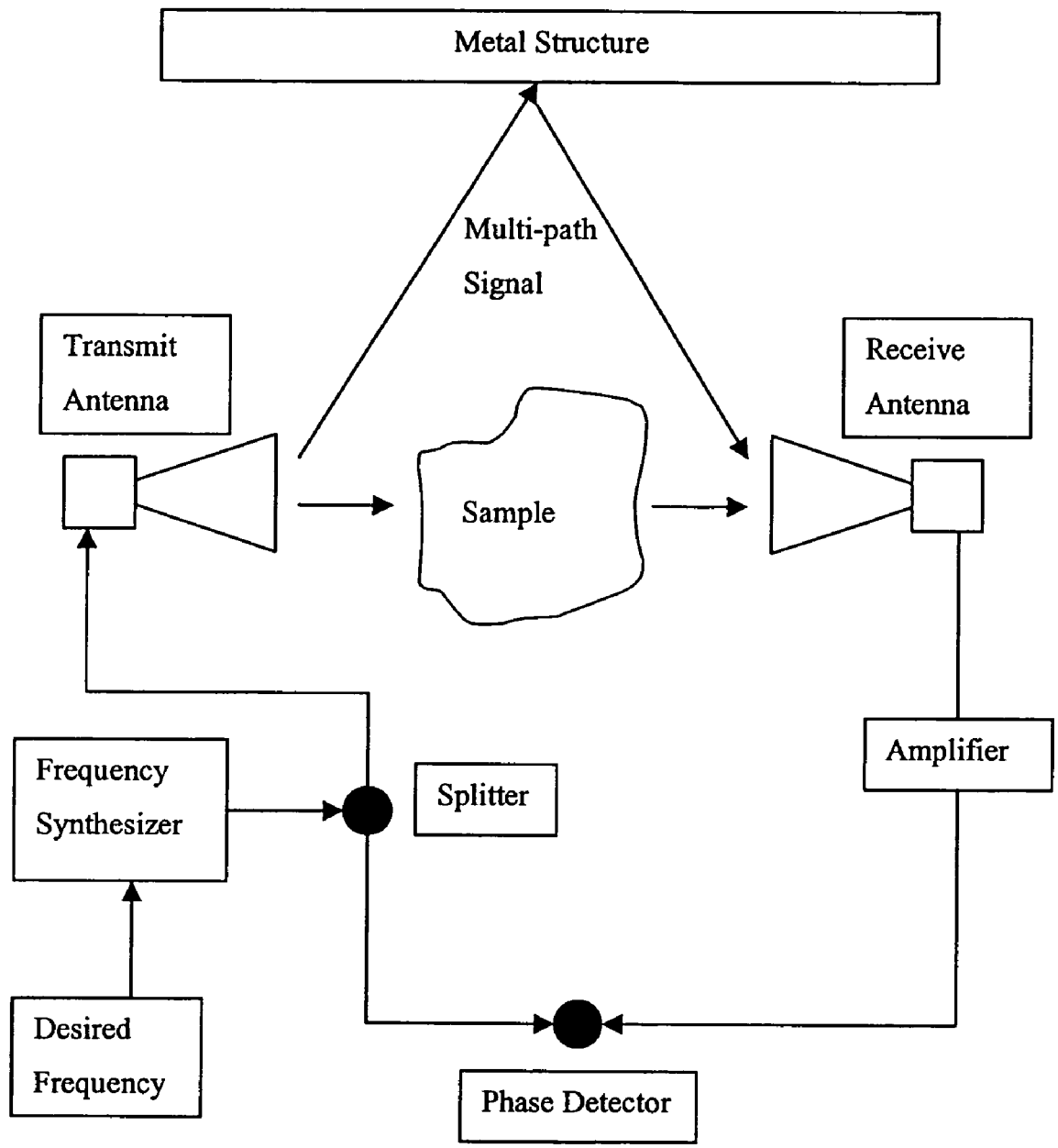
FIG. 9 is a block diagram of an alternative typical configuration of the hardware used in the moisture sensing system of this invention.

This invention is based upon the principles of electromagnetic radiation propagation through free space and a dielectric, the dielectric being the material under test. Electric and magnetic propagation are characterized by Maxwell's equations, as published by Maxwell in 1873. For plane waves in a general lossy medium, Maxwell's curl equations can be written as:

$$\nabla \times E = -j\omega \mu H \quad (1)$$

$$\nabla \times H = j\omega \in E + \sigma E \quad (2)$$

where
$\nabla :=$ Gradient Operator
$E :=$ Electric Field (V/m)
$H :=$ Magnetic Field (A/m)
$j :=$ complex plane
$\omega :=$ frequency (rads/s)
$\in :=$ Permittivity of medium
$\mu :=$ permeability of medium
$\sigma :=$ conductivity of medium.

Utilizing the complex representation of the permittivity $$\in = \in' + j \in'' \quad (3)$$

provides the following definition for the complex propagation constant for the medium as $$\gamma = j\omega[\mu \in'(1-j \tan \delta)]^{1/2} \quad (4)$$

where
$\tan \delta = \in''/\in' :=$ loss tangent.

For low loss materials where the loss tangent is very much less than one, then a good approximation is $$\gamma = j\omega[\mu \in']^{1/2} \quad (5).$$

Using this relation we see that a positive traveling wave has the propagation factor of the form (Pozar, 1998):

$$E_x(z) = e^{-\alpha z} \cos(\omega t - \beta z) \quad (6).$$

Where
$E_x(z) :=$ Electric field in the x direction as a function of distance z.
$Z :=$ propagation distance from the source in meters
$\omega :=$ wave frequency in radians per second
$t :=$ time in seconds
$\alpha :=$ attenuation constant in nepers per meter
$\beta :=$ phase constant $= k = \omega[\mu \in']^{1/2}$.

When applying these relationships for agricultural products, it should be noted that the magnetic permeability is typically immeasurably different from that of air. Thus, from this relation, by measuring the phase constant at a single frequency, a direct measurement of the real portion of the permittivity of the material is obtained, which permittivity in turn is known in the art to have a high correlation to the water content of the material at a given density.

The next fact of interest is that the permittivity of water and agricultural products such as seedcotton or cotton lint are not fixed, but vary with regards to frequency. The change in the dielectric constant of water from low frequency to 1

GHz only drops from 80.37 to 80.0 yielding only about a 0.5% change. The change in the dielectric constant of water from 1 GHz to 10 GHz drops from 80.0 to 75.6 or about a 1% change. At this point it should be noted that the slope of the dielectric constant of water starts to change much faster with a huge increase in the slope above 3 GHz. In contrast to the relatively stable dielectric constant of water below 2 GHz, the dielectric constant of agricultural materials has a much larger percentage change of about 25% when changed over this same frequency range. Utilizing a commonly accepted dielectric mixing model from those skilled in the state of the art, equation 7, we see that the combined permittivity due to water and the cotton becomes:

$$\in' = [V_m \in'^{1/2}_m + V_w \in'^{1/2}_w]^2 \quad (7)$$

where $V_m$:=volume fraction of material
$\in'_{mn}$:=dielectric constant of material at frequency n
$\in'_{wn}$:=dielectric constant of water at frequency n.

Now using equation 7 in conjunction with the phase constant relation provides a relation between the phase constant and the combined permittivity of cotton and water (equation 8):

$$\beta = \omega[\mu \in']^{1/2} = \omega[\mu[V_m \in'^{1/2}_m + V_w \in'^{1/2}_w]^2]^{1/2} \quad (8).$$

The equations for the 1$^{st}$ derivative or difference of equation 8 taken at two frequencies, provide (equation 9):

$$\beta_2 - \beta_1 = \omega \mu^{1/2}[[V_m \in'^{1/2}_{m1} + V_w \in'^{1/2}_{w1}]^2 - [V_m \in'^{1/2}_{m2} + V_w \in'^{1/2}_{w2}]^2] \quad (9).$$

At this point note that the effective change of the dielectric constant for the material is much larger than that for the water. This observation then provides an approximation to the equation by letting $\in'_{w2} = \in'_{w1}$; thus equation 8 can effectively rewritten in the approximate form (equation 10) which shows that the difference in the phase constant provides a direct correlation to the density (this equation is only valid for frequencies below 2-3 GHz):

$$\beta_2 - \beta_1 = \omega \mu^{1/2}[V_m(\in'^{1/2}_{m2} - \in'^{1/2}_{m1})] \quad (10)$$

This theory was then tested to obtain experimental data of the slope of the "phase constant" or delta-phase measurements versus moisture and density of cotton lint bales for frequencies ranging from 1.85 GHz and 2.2 GHz yielding a coefficient of determination between the delta-phase measurement and the mass measurement for an $r^2 = 0.78$ (FIG. 1). To further illustrate the dominance of the mass effect on the delta phase, the coefficient of determination between delta phase and the moisture produced a very low of $r^2 = 0.44$ (FIG. 2). This data illustrates that the delta phase measurement as detailed in equation 10 can be used to provide a measure of the density of the material that is largely independent of the moisture content. It should be noted here that this is not a perfect relation as a higher coefficient of determination of $r^2 = 0.95$ was calculated by correlating the delta phase to the moisture and density product, i.e. mass*moisture (FIG. 3). This indicates that the highest accuracy can be achieved through the determination of density through standard means. However in situations where this is not possible this technique provides a sound alternative.

Prior art patents have previously discussed at length the need to resolve the integer rollover portion of the phase delay. In contrast, in this portion of the invention that utilizes delta-phase measurement, the integer rollover determination is not a requirement as it is subtracted out when calculating the derivative. Thus, the density measurement by delta-phase requires no calibration, and no further processing or attenuation measurements in order to calculate the integer rollover of the phase delay. Additionally for the moisture determination from the instrument corrected phase delay measurement, it has been found that at these lower microwave frequencies, that a frequency can be optimally selected, for a given moisture content range, to provide over 120 degrees of phase delay but less than 180 degrees of phase delay, thereby providing good resolution in moisture determination while at the same time avoiding the rollover issue.

Once the density has been determined to a reasonable accuracy, the next portion of the invention is the measurement of the phase constant of the material only in order to estimate the moisture content. This is advantageous over the state of the art as this invention does not require the use of attenuation measurements which requires a different processing technology and a much higher frequency as attenuation measurements at the lower frequencies of this invention have almost no correlation to moisture content. The much lower frequency operation of this invention results in a less expensive system by reducing components count, by eliminating unnecessary measurements, as well as allowing the use of lower cost lower frequency components. A third advantage is that the radar cross-section of a bail tie at these lower frequencies is virtually invisible. By utilizing a much lower frequency than the prior art, the system is able to reduce the radar cross section by operating in the very low portion of the Raleigh region. To illustrate, consider the prior art wavelength of 8 GHz is 1.475 inches. The radar cross section of a 0.125 inch bale tie is nearly 0.1 at this higher frequency. This makes the bale tie a strong reflector at this high microwave frequency yielding a significant number of spurious reflections that will interfere with the desired measurement. At the lower microwave frequencies of this invention, the radar cross section is less than 0.0001. Thus, by utilizing the lower microwave frequencies practiced by this invention, the system provides a 60 dB advantage over the prior art in rejecting bale tie interference. A fourth advantage is that at these lower frequencies, phase roll-over never occurs, thereby eliminating yet another requirement of the prior art, the phase roll-over discriminator which was illustrated in many of the previously discussed patents of Meyer, Nelson, and Moshe.

While phase roll-over is not an issue for density measurement, as previously discussed, it is an issue for the moisture estimation when performing a phase only measurement. In regards to the prior art, this invention differs in that the moisture measurement is derived solely from the phase measurement whereas the prior art derives the measure from the attenuation or a ratio of attenuation to the phase. In the moisture measurement portion of the invention, the measurement is performed by taking an air reference to center the measurement and remove the effects of the antennas, cables, etc. The system then takes a single or multiple measurements of the material under test at one or more frequencies and measures the difference between the air reference phase constant and the material under test's phase constant. Additional frequencies are helpful in providing increased accuracy in the determination of the instrument corrected phase delay between the material under test and the air reference. This is due to error's that occur in the phase measurement around zero and 180 degrees. As the system must measure both an air reference as well as varying bale measurements, the ideal frequency is not known ahead of time. Thus, the use of multiple frequencies allows for either an interpolation to the desired frequency or enables a correction to a set frequency to remove errors caused by poor phase measurements at these extreme angles. The system as described provides a calibrated, with respect to an air reference, phase delay measurement of the cotton bale or other test material. By knowing this phase delay and the frequency it is then possible to determine the phase constant of the material, or equivalently, the phase velocity or propagation delay due to transmission through the material. This technique when corrected for the weight by either the previously discussed delta-phase measurement technique or through the use of a scale or other density determining device, can accurately measure the moisture content (FIG. 6) to within the accuracy of the gravimetric oven drying standard moisture determination method. Alternative density determining devices include conventional systems such as scales, air resistance to flow, and ultrasonics.

The preferred embodiment for implementing this invention consists of a microwave sensor or microwave imaging device, shown in FIG. 8, that is designed to generate a range of microwave frequencies using a frequency synthesizer 4 in which part of the signal is passed through a sample 15 or, when the sample is absent, through air 26 and the other part of the signal is directed as a reference signal to a phase detector 11. This will provide a measurement of the relative phase delay of either the sample or of air. The frequency synthesizer 4 is shown in detail in FIG. 7. It comprises of a phase-locked loop (PLL) 27 containing a Voltage-Controlled Oscillator (VCO) 28, a low pass filter (LPF) 29, a phase detector (PD) 30, and a loop frequency divider N 31. Also included is a fixed clock generator 32, a frequency divider M 33. The desired output frequency is provided through port 34. The output frequency is determined by the clock frequency divided by M multiplied by N. These N and M parameters are set forth by the controlling processor as shown in FIG. 8, connected to the frequency synthesizer 4 by a control bus 5. This provides frequency synthesis without the necessity of utilizing mixers and subsequent filters to remove the mirror frequencies produced by the mixers. It also provides the system with the ability to rapidly obtain measurements at multiple frequencies. The signal, as generated from the frequency synthesizer, is then split into two paths by a splitter 7, one, hereafter known as the reference path, proceeds directly to a phase detector 11 whereas the other path, hereafter known as the sample path, proceeds either directly to an antenna 13 or proceeds through one or more amplifiers 8 that are placed either before the transmit antenna or after the receiving antenna 20 thereby providing some gain to the transmitted signal to allow the signal to more easily pass through rf absorbing materials such as wet cotton 15. The signal passing through the sample material, the receiving antenna, and any subsequent amplifiers, is then presented to the phase detector 11 port A via conduit 21. The other feed from the splitter 7 is also Ted to the phase detector 11 through port B using conduit 10. If the signal strength of port B is too great in comparison to signal delivered at port A, a signal attenuator 35 shall be installed on feed 10. It should further mentioned that antennas 13 and 17 can be additionally protected from reflected signals using radio wave absorbing materials 14 and 18 respectively. The system also includes the processing unit 1 also referred to as PU, consisting of a central processing unit also referred to as CPU containing memory, signal drivers, signal receivers, data ports. The PU also contains display indicator 2, data entry keys 3, a power supply 24, connecting power cable 25, and interface wires to the phase detector 22 and 23 through which the phase and the signal strength voltages are fed to the CPU, and other associated components.

In practicing the invention, through the execution of preprogrammed sequence of commands by the CPU, the system performs a series of measurements in a frequency sweep, at each frequency the synthesizer is allowed to stabilize and lock onto each target frequency before starting a measurement cycle, from starting frequency f1 to end frequency fn at step increment fstep totaling n different frequencies, measuring and storing relative phase delay measurements Phi, one for each of the discrete frequencies fi in the sweep. The sweep is executed twice, one sweep as air reference, without the presence of the material under test, storing the relative phase delay measurement in an array Phairi, and another sweep of the same frequencies fi's with the material under test or bale of cotton, positioned between the transmitting and receiving antennas, measuring and storing the relative phase delay measurements in an array Phmati. The system processor 1 then subtracts the relative phase delay measurements of the air reference Phairi from the measurements of the cotton bale or material Phmati, obtaining the calibrated phase delay PHcali for each of the n frequencies fi in the frequency sweep. The relative phase delay differences PHcali obtained by this calculation is the corrected or calibrated phase delay for the material under test. Each frequency sweep is taken as a single physical point of measure of the material under test at a rate sufficient to provide an equivalent static measurement should the material under test be in motion on a conveyor belt or other conveying system. Upon obtaining the corrected phase delays, the phase delays are then unwrapped across the frequency sweep such that the calibrated phase delays form a continuous curve which is the unwrapped corrected phase delay. Next, taking the difference of the highest and lowest frequency's unwrapped corrected phase delay to produce a measure of the slope or derivative of the unwrapped corrected phase delay to yield a delta phase delay measure. This delta phase delay measure is then used to calculate the density of the material. The calibrated phase delay of at least one of the frequencies fi are then used to calculate the moisture contents in conjunction with the density of the cotton bale or sample under test, using a calibration table or equation relating the density and weight to moisture contents.

The best frequency bands to utilize for these measurements is dictated by the path length and moisture content of the sample material with the choice dictated by choosing the highest frequency in which good transmission through the sample is still obtained and the phase delay, across the expected range of samples, varies by less than 360 degrees. This provides sufficient accuracy while minimizing the requisite circuitry. Other considerations into the choice of frequency range is that the frequency should be kept below 2.5-3.0 GHz to minimize the non-linearity in the delta-phase mass sensing measurement as well as to maintain a minimal radar cross-section of the metal bale ties. The best choice of frequency for use in cotton bale measurements turns out to be in the 1.5 GHz to 2.0 GHz region with the transmission passing through the narrowest dimension of the cotton bale; however it should be noted that it will also work with higher frequencies by adding amplifiers as well as lower frequencies at reduced accuracies and with the necessity of much larger antennas. FIG. 9 details the preferred topology of the system with a minimalist configuration to reduce component count and cost.

The preferred antenna choice is a very directional broadband antenna such as a microwave horn. While the system preference is a microwave horn, it should be noted that other antennas could also be used such as patch antennas, log-periodic, parabolic dishes, yagi antennas etc. The directional nature is important to reduce the effects of multi-path interference which is generally an issue in enclosed metal structures such as cotton gins and module feeder storage sheds.

The unique configuration of this system utilizes direct frequency synthesis and direct frequency detection which provides a unique economic advantage as it provides a much simpler and lower cost system than has been traditionally used in the prior art heterodyning systems, as it avoids mixers and filters on both the transmit as well as the receive side not to mention the cost of research and development of the requisite circuitry required to perform the traditional heterodyning frequency synthesis and subsequent heterodyning and filtering on the receive side. This results in the ability of the manufacturer to produce a system for the consumer that is much more economical and competitive without loss of performance. It should be noted that because of the lack of mirror frequencies that are generated by heterodyning systems and then subsequently only partially removed through filtering, that this system typically has a better performance that the traditional heterodyning systems do.

The system algorithm for calculating the moisture level in the bale or sample under test utilizes the following process: The system performs phase measurements at discrete frequencies fi through air and then through the cotton bale. Then calculates the calibrated phase constant PHcali for each of the frequencies by subtracting the phase constants of air measurements from those of the sample measurements. The total mass of the sample is determined by calculating the calibrated phase difference, defined as delta phase, between two predetermined frequencies k and l. The correlation between delta phase measurements and actual mass of the sample can be determined separately and summarized in a calibration table of equation before hand and used as a given mass determination formula for this process. FIG. 1 demonstrates the correlation between delta phase measurement and actual mass of the sample. Then selecting a single calibrated phase constant at frequency j, Phcalj, the final moisture content in the sample is determined from predetermined calibration table containing all combination of moisture levels as function of calibrated phase and mass densities of the type of sample used in the process. Alternately, a mathematical expression can be derived.

The system scans a sample across a frequency band starting at frequency 1 (1.7 GHz in this case) through frequency 2 in steps of a delta frequency of which a preferred step is 500 kHz or less so as to provide enough samples to resolve the phase roll-overs in the raw phase measurement. At each frequency a measurement is taken between the phase of the reference signal and the signal that is transmitted through the sample (see FIGS. 9, 10) yielding a corrected phase measurement between these two signals. The closeness of the frequency spacing between each reading is required as it is necessary to accumulate the total phase delay between the starting frequency and the ending frequency as this provides the unwrapped phase delay from the starting frequency to the ending frequency. The slope of the unwrapped phase delay is then calculated either by utilizing the total unwrapped phase delay between the starting frequency and the ending frequency or an improvement would be to perform a least squares calculation of the slope utilizing all of the intermediate frequencies to help reduce the noise in the final measurement of the slope. Other noise reduction techniques include taking multiple readings at each frequency which are taken at a high enough sampling rate to ensure that upon averaging, that most of any 60 Hz noise that is in the dc phase difference signal can be removed from the delta phase measurement. Preferred sampling rates are above 200 Hz over a time span of 0.1 seconds. These readings are then combined via averaging to form one corrected phase reading for that frequency. This process is then repeated for each frequency in the scan list to obtain a frequency sweep of corrected delta-phase constant measurements across the range from 1.7 GHz to 1.85 GHz (or higher if more accuracy is desired). The frequency sweep of delta-phase measurements is then analyzed to calculate the slope $\phi$ between the frequency and the delta-phase readings which, as discussed earlier is related to the permittivity constant of material. The slope $\phi$ is utilized through calibration equations to obtain a measurement of the density of the material.

This same data is also used to obtain a measurement of the moisture content. In use, the corrected phase measurements are used to interpolate the most accurate corrected phase measurement for a given target frequency. This target frequency and phase measurement are then used along with a calibration equation to predict the moisture content. In this manner, this technique predicts both the moisture content (times weight) as well as the density of the material under test.

The process and apparatus of the invention may be used to determine the moisture content of a wide variety of materials. Non-limiting examples of such materials include cotton (seed cotton and/or lint), grass, hay, tobacco, timber, lumber, and paper pulp, and particularly cotton bales.

The following examples are intended only to further illustrate the invention and are not intended to limit the scope of the invention which is defined by the claims.

EXAMPLE 1

A preferred system was constructed for measuring the moisture of cotton bales. This system assumes a cotton bale density such that an industry standard Universal Density bale (UD bale) weighs approximately 500 lbs, and a path length of the material is 21 inches (the short dimension of the UD bale through which the signals will be transmitted).

The following steps were performed two times; once with no material between the antennas (air-instrument propagation delay measurement) and again with the cotton bale or material under test located between the two antennas (material plus air-instrument measured propagation delay). After obtaining both the air propagation delay and the material plus air-instrument propagation delay the final measurement is the difference between these two readings. It is this final measurement that provides a measure of the moisture content of the material for a given material density and path length. In situations where the material and path length are well controlled, no other information is required, such as is the case for moisture measurement of cotton bales. However, in other situations or to improve the accuracy both the density and the path length can be obtained through conventional means to improve the moisture measurement.

In this system, further improvements can be achieved by optionally repeating the measurement in a series of tests. In each test a different control voltage repetition rate is utilized. The results of each of these tests is then averaged to obtain the final measurement.

Step 1: Generate a stable single frequency microwave sinusoidal signal 0 at a frequency of 1.75 GHz. The preferred method of generating this signal is to utilize a VCO and phase-locked loop techniques in conjunction with an oven-stabilized crystal reference oscillator. In this manner an extremely stable signal is generated directly at the frequency of interest.

It should be noted that any microwave frequency can be utilized, however for this application there is a very narrow range of suitable frequencies. This range is limited due to the use of metal bale ties that are used to bind the cotton bales. At frequencies below 2.5-3.0 GHz, these ties present a very small radar cross-section and as such the ties do not create spurious reflections when the frequencies are kept preferably below 2.5 GHz. Other issues influencing the optimum range include the expected range of moisture contents. As this is primarily a phase measurement technique, at a certain upper frequency a roll-over in the phase measurement will occur making the higher moisture contents appear to the sensor to be low moisture. This can be avoided by choosing a frequency such that the roll-over occurs at a high moisture content beyond the range of expected use. Thus, for use in cotton bale packaging, the expected range is from 4% to 10% moisture content with a target moisture content of 7.5% and as the cotton lint packaging systems are standardized on the 227 kg universal density bale (UD bale) with lint density of 0.4 gm/cc, and the system transmits through the short section of the cotton bale (0.5334 m thick) this gives the optimum operating frequency range occurring at 1.75 GHz through 1.85 GHz. While this is the optimum, it should be recognized that the system will work at lower frequencies with reduced accuracy and the requirement of larger and more expensive antennas. At frequencies above 2.2 GHz the system will also work at an increased accuracy with the understanding that the range of moisture measurement will be reduced before the phase roll-over occurs (as discussed previously). One such suitable phase locked loop controller is National Semiconductors LMX2311U. This packaged component takes as an input the reference oscillator as well as the output frequency that is fed back to the controller for control purposes. In addition to this chip it is required that an external unity gain analog phase-locked loop filter is placed between the output control voltage from the LMX2311U. For the preferred target frequency as discussed previously with a step frequency between channels of 200 kHz, one such suitable such filter has a corner frequency occurring at 10 kHz (Valkenburg, M. E., 1982. Analog Filter Design. Holt, Rinehart and Winston, New York). The output from this loop filter is then used as the control voltage to the voltage controlled oscillator (VCO) that will be used to generate the microwave signal directly.

Step 2: Apply the control voltage of step 1 to the microwave voltage controlled oscillator (VCO). This VCO will have a specification rating such that this VCO will generate a range of frequencies ranging 1.73 GHz to 1.75 GHz for the applied control voltage input as previously discussed in step 1, hereafter known as signal 0, when the voltage control signal of step 1 is input to this VCO. One such suitable VCO is the 790-1750t VCO manufactured by VariL Corp although any other digital or analog means to generate this signal would be acceptable.

Step 3: Provide either a loss-less or resistive T junction power divider (Pozar, D. M., 1998. Microwave Engineering. $2^{nd}$ Ed., New York: Wiley) to split the signal into two signals; signal 1 and signal 2. Signal 1 will be used to transmit the signal through the cotton bale and signal 2 will be used as the internal reference signal.

Step 4: Convey signal 1 to an amplifier by means of a low loss coaxial cable.

Step 5: Convey signal 2 to a phase detector (microwave mixer or equivalent phase detector), preferably a low noise version such as a double-balanced mixer (Pozar, ibid).

Step 6: Convey amplified signal 1 to a microwave horn or other type of directional antenna with a preferred signal focusing or gain of at least 10-20 dB (Balanis, C. A. 1982. Antenna Theory, analysis and design. New York, Harper & Row). This horn or antenna is to be located on one side of the cotton bale or other material under test such that the majority of the signal is transmitted through the cotton bale or other material under test. It should be noted that this technique will work with any type of antenna and that the use of directional type of antenna is specified in order to achieve the best possible performance.

Step 7: Place a receiving antenna of similar design to the transmitting antenna utilized in step 6, on the opposite side of the cotton bale or material under test. This antenna should be oriented such that the best reception of the transmitted signal will be received (Balanis, ibid).

Step 8: Adjust received signal 1 to have the same amplitude as reference signal 2 through an automatic gain amplifier and convey received signal 1 by means of a coaxial cable to the double-balanced mixer of step 5.

Step 9: Mix the received signal 1 with signal 2 in the double-balanced mixer of step 5 and step 8 to form relative phase delay signal 3. Note, the process of mixing two signals of the same frequency together produces a dc measure of the phase difference between the two signals (assuming that the amplitudes of the signals are equal).

Step 10: Convey signal 3 by means of coaxial cable to an analog low pass filter to form a filtered version of signal 3 hereafter labeled signal 4. In the preferred embodiment the filter will be constructed to have the following specifications; the corner frequency is less than 1 kHz, the passband ripple is less than 3 dB, and the stop band attenuation is greater than −40 dB in relation to the passband signal (Valkenburg, ibid). It should be noted that the only true requirement is that the stop band of the filter be such that the frequency components that are located above two times the desired sampling frequency are rejected in order to avoid aliasing of these frequency components into the signal during the digitization stage that will be performed in a subsequent step (Porat, B. 1997. A course in digital signal processing. New York, John Wiley and Sons, Inc.). An optional and desirable additional filter can be added to remove 60 cycle noise. One of the benefits of utilizing this filter is to reject 60 Hz noise that is easily picked up by the antenna system in an industrial environment such as a cotton gin processing plant.

Step 11: Convey signal 4 to an analog to digital converter. This a2d must sample signal 4 at a frequency that is greater than two times the stop band frequency of the analog low pass filter that was utilized in step 10 (Porat, 1997). For this example the preferred sampling frequency is greater than 4 kHz. This analog to digital captured signal in digital form (data) will hereafter be referred to as signal 5.

Step 12: Apply a digital low pass filter to the data that comprises signal 5. This digital filter will be designed with the goal of obtaining a single integrated value for a series of scans at the specified frequency as obtained in step 1. For this example; this digital low pass signal will be constructed with the following specifications; the first corner frequency will be 0.01 pi, the second corner frequency will be 0.02 pi, the stop band will be attenuated to below −40 dB in relation to the pass-band, and the preferred roll-off of the corner frequencies will be greater than minus 80 dB/decade (Porat, ibid). It should be noted that while a band pass filter will provide the best performance; a low pass filter could also be utilized. It should further be noted that steps 11 and 12 could alternatively be performed all in the analog domain at the cost of loss of flexibility and stability of the filtering operation.

Step 13: The output digital waveform from step 12 is then analyzed digitally to determine it's DC Voltage value. This DC Voltage value of this signal is the measurement of the phase delay of the propagated signal 1.

Step 14: Once the final filtered DC Voltage phase delay value has been obtained from step 13 this value can be utilized to calculate the propagation delay or time it takes for signal 1 to be transmitted through the material under test. This propagation delay is typically quantified by the phase velocity or the phase constant of material. Hence, once any or all of these parameters has been determined, it can be used to determine the permittivity of the material from the following relations:

$$\beta = \omega/v_p \quad (11)$$

$$\theta_{test\_air} = \theta_{instrument} + \theta_{air} \quad (12)$$

$$\theta_{test\_mat} = \theta_{instrument} + \theta_{mat} \quad (12a)$$

$$\theta_{mat} = \theta_{test\_mat} - \theta_{test\_air} \quad (12b)$$

$$\beta = (2\pi n + \theta_{mat}) \quad (12c)$$

$$v_p = c/\sqrt{u_r * e_r} \quad (13)$$

where

β:=phase constant of material under test (rads/m)
L:=signal propagation path length {thickness of material under test} (m)
ω:=frequency of signal 1 (rads/s)
θ:=relative phase between the reference signal 2 and the transmitted signal 1 (rads)
$\theta_{instrument}$:=phase delay of the internal reference signal 2 (rads)
$\theta_{test\_air}$:=relative phase delay of signal 1 to signal 2 as measured with only air (rads)
$\theta_{test\_mat}$:=relative phase delay of signal 1 to signal 2 as measured with material (rads)
$\theta_{mat}$:=phase delay of signal 1 due to the material (rads)
$\theta_{air}$:=phase delay of signal 1 due to the air (rads)
$e_r$:=permittivity of material under test (F/m)
$v_p$:=phase velocity (m/s)
c:=velocity of light (m/s)
t:=transmit time for the wave (signal 1) to propagate through the material (s)

Noting that the permeability of cotton and other biological products are essentially equivalent to that of air equation 11 can be simplified to equation 13b.

$$v_p = c/(e_r^{1/2}) \quad (13b)$$

$$t = L/v_p \quad (14)$$

In the interest of quantifying the material under test independently of the system, it is necessary to take an air reference to provide a zero reference point for the system.

It is a goal of this invention to provide a measurement of material that is independent of geometry and therefore the path length of the propagation needs to be accounted for in addition to the internal delays that occur in the transmission of the signals within the instrument. The best way to perform this is to characterize the material in terms of permittivity rather than a direct moisture calibration (though this is also easily done). After obtaining the permittivity of the material, one can then relate measured permittivity to the moisture content of the material (assuming either a knowledge of the material's density or obtaining the density by conventional means). Utilizing the basic relations from equations 11-14, we arrive at the function that predicts the permittivity of material. For cotton bales with the measurement performed in the configuration as previously discussed, the integer phase delay number "n" as used in equation 15 is 3. For other lengths and or materials this integer constant is easily determined from a knowledge of the phase constant of material. It should be noted in equation 15 that the air reference phase measurement is subtracted from the material phase measurement. This is done to remove the effects of the instrument from the measurement thereby providing a zero reference for the technique and thereby provides a true measure of the materials propagation delay. Additionally it should also be noted that the path length of the material is also a part of equation 15 and as such it is removed from the measurement in this manner thereby providing a true measure of the material's permittivity.

$$e_r = [c(2\pi n + \theta_{mat} - \theta_{air})/(L(\omega))]^2 \quad (15)$$

Once the permittivity of the material under test is known, a function that relates the permittivity to the density and moisture of the material can be formulated from experimental data for the desired moisture and density ranges at the frequencies of interest. One such equation that can be utilized for this purpose for cotton is detailed in equation 16 (though it should be recognized that many other forms could also be used with similar results):

$$\% M.C. = [(5.397(e_r^{1/2})/\rho) - (5.193/\rho)] + 0.8844 \quad (16)$$

where
ρ:=density of the material (gm/cc).

In this system improved accuracy can be achieved by repeating the measurement over a short range of frequencies and discarding any phase values that are near zero or one-hundred eighty degrees (areas of least accuracy for the relative phase measurement) and then averaging the remaining values to obtain a better estimate of the true relative phase delay for both the air reference phase delay and the material phase delay measurement.

In addition to moisture determinations, the system of this invention may also be used to determine the density of test materials. As density is not always controlled it is another aspect of this invention to provide a measure of the density that is independent of moisture and can be performed with the same instrumentation by extending the measurement protocol. This can be achieved with the following additional steps:

Step 15: The measurements detailed in steps 1-14 are repeated at steadily increasing frequencies to obtain a series of measurements that range from 1.75 GHz through 2.2 GHz (or more). This is done to obtain phase delay measurements for both the air reference as well as the material under test, thus at each individual frequency the material phase delay is corrected to the air reference as detailed in equation 17.

$$\theta_{cor\_mat} = \theta_{mat} - \theta_{air} \quad (17)$$

where
$\theta_{cor\_mat}$:=phase delay of the material corrected for the air reference The frequency step to take between each phase measurement, as outlined in steps 1-14, is to be limited to less than 5 MHz with better results being obtained with much smaller steps. In summary steps 1-14 are performed at 1.75 GHz, then the frequency is increased to 1.76 GHz and steps 1-14 are performed again and so on until the system reaches 2.2 GHz.

Step 16: Once this series of corrected phase delay measurements has been obtained from step 15, the phase is unwrapped to remove any roll-overs as the signal changes from −180 to +180 (the phase delay measurement only provides a reading between −180 to +180). To illustrate, if the corrected phase delay at 1.75 GHz is −179 degrees and the corrected phase delay at 1.80 GHz is +179, then this reading is changed to −181 degrees thereby removing the phase roll-over from −180 to +180. In addition to this phase unwrapping, the integer "n" of equation 7 is incremented at each rollover from −180 to +180 and decremented from each shift from +180 to −180. In this way the technique only requires knowledge of the initial integer "n" phase delay at the starting frequency and can calculate the new "n" for each additional frequency step as detailed in step 15. Alternatively, as the final step 17 is a derivative calculation any arbitrary "n" value can be used for the initial "n" at the starting frequency as it will be subtracted out in the process of calculating the derivative.

Step 17 (optional): Utilizing the corrected phase delay measurement and it's corresponding integer "n" from step 16, the permittivity for each frequency step is calculated.

Step 18: Utilizing the calculated permittivity from step 17 (or the unwrapped phase measurements from step 16), the slope of the permittivity versus frequency is calculated (or alternatively unwrapped phase versus frequency hereafter known as the delta-phase measurement). It has been found that this slope of the permittivity versus frequency or delta phase measurement is highly correlated to the density with little correlation to moisture. An example that utilizes the delta phase to calculate density is detailed in equation 18 (unwrapped phase starts at "$2\pi n$" and continues in the negative direction to signify an increase in the phase delay as the frequency increases).

$$\rho = -0.0042 d\theta/df + 0.1698 \quad (18)$$

where $\rho$:=density of material (gm/cc)

$d\theta/df$:=delta phase measurement.

It is understood that the foregoing detailed description is given merely by way of illustration and that modifications and variations may be made therein without departing from the spirit and scope of the invention.

REFERENCES

Anthony, W. S. 1990. Computerized gin process control. Applied Engineering in Agriculture, 6(1):12-18.

Anthony W. S. and R. K. Byler, 1994. Status of gin process control systems. Proc. Beltwide Cotton Conf., San Diego, Calif. 5-8 Jan. 1994 Natl. Cotton Counc. Am., Memphis, Tenn.

R. K. Byler and W. S. Anthony, 1995. Development of a moisture sensor for gin use. Proc. Beltwide Cotton Conf., San Antonio, Tex. 4-7 Jan. 1995. Natl. Cotton Counc. Am., Memphis, Tenn.

R. K. Byler and W. S. Anthony, 1997. Measurement Concepts in a gin process control system, Proc. Beltwide Cotton Conf., New Orleans, La. 7-10 Jan. 1997. Natl. Cotton Counc. Am., Memphis, Tenn.

Kraszewski, A. W., S. Trabelsi, and S. O. Nelson, 1996. Wheat Permittivity Measurements in Free Space, Jo. Microwave Power and Electromagnetic Energy 31(3): 135-141.

Kraszewski, 1988. Microwave Monitoring of Moisture content in Grain-further considerations, Jo. Microwave Power and Electromagnetic Energy 23(4):236-246.

Nelson, S. O., A. W. Kraszewski, S. Trabelsi and K. C. Lawrence, 2000. Using Cereal Grain permittivity for sensing moisture content, IEEE Trans. Instrumentation and Measurement 49(3):470-475.

Trabelsi, S., A. W. Kraszewski, and S. O. Nelson, 2001. New Calibration Technique for Microwave Moisture Sensors, IEEE Trans. Instrumentation and Measurement 50(4): 877-881.

Pozar, D. M., 1998. Microwave Engineering. John Wiley and Sons, Inc. New York. pp. 16-20.

We claim:

1. A process of determining the moisture of a material comprising:

producing two or more primary microwave signals with a frequency synthesizer, said primary signals having different frequencies, splitting each of said primary signals to provide a first and second microwave signal from each single primary signal generated by the frequency synthesizer, said first signals to be transmitted through the material or through air only, and said second signals comprising internal reference signals, transmitting said first signals through at least a portion of said material, receiving at a receiver said first signals which have passed through said material, transmitting said first signals through air only, receiving at a receiver said first signals which have passed through air only, measuring the phase difference between each said second signal and each said first signal which has passed through air only, wherein said second signal is at the same frequency as said first signal which has passed through said air, and determining therefrom the air reference phase delay at said different frequencies, measuring the phase difference between each said second signal and each said first signal which has passed through said material, wherein said second signal is at the same frequency as said first signal which has passed through said material, and determining therefrom the material phase delay at said different frequencies, calculating the difference between said air reference phase delay and said material phase delay to determine the instrument corrected material phase delay at those different frequencies, obtaining the weight or density of said material, and calculating the moisture content of said material from said instrument corrected material phase delays and the weight or density of said material;

further comprising determining a delta phase measurement from said corrected material phase delay at the different frequencies, and wherein said weight or density of said material are determined from said delta phase measurement;

wherein said delta phase measurement is determined from the derivative of said instrument corrected material phase delays at the different frequencies and the determination of said delta phase measurement comprises;

unwrapping said instrument corrected material phase delay to provide a continuous curve of instrument corrected phase delay versus frequency, and determining therefrom the unwrapped instrument corrected phase delay, and determining the derivative from the unwrapped instrument corrected phase delay versus frequency to produce said delta phase measurement.

2. The process of claim 1 wherein said two or more primary microwave signals are generated sequentially.

3. The process of claim 1 wherein said material is selected from the group consisting cotton, hay, grain, tobacco, timber, lumber, and pulp.

4. The process of claim 1 wherein said material comprises a cotton bale.

5. The process of claim 1 wherein the determination of said delta phase measurement comprises:

unwrapping said instrument corrected material phase delay to provide a continuous curve of instrument corrected phase delay versus frequency, and determining therefrom the unwrapped instrument corrected phase delay, and calculating the difference between the highest and lowest frequency's unwrapped instrument corrected phase delay, and determining therefrom the derivative of the unwrapped instrument corrected phase delay versus frequency to produce said delta phase measurement.

6. The process of claim 1 further comprising:

obtaining the transmission path-length of said first signal through said material, calculating the moisture content from a calibration equation that utilizes said transmission path-length, said instrument corrected material phase delay, and said density or weight.

7. A process of determining the density or weight of a material comprising:

producing two or more primary microwave signals with a frequency synthesizer, said primary signals having different frequencies, splitting each of said primary signals to provide a first and second microwave signal from each single primary signal generated by the frequency synthesizer, said first signals to be transmitted through the material or through air only, and said second signals comprising internal reference signals, transmitting said first signals through at least a portion of said material, receiving at a receiver said first signals which have passed through said material, transmitting said first signals through air only, receiving at a receiver said first signals which have passed through air only, measuring the phase difference between each said second signal and each said first signal which has passed through air only, wherein said second signal is at the tame frequency as said first signal which has passed through said air, and determining therefrom the air reference phase delay at said different frequencies, measuring the phase difference between each said second signal and each said first signal which has passed through said material, wherein said second signal is at the same frequency as said first signal which has passed through said material, and determining therefrom the material phase delay at said different frequencies, calculating the difference between said air reference phase delay and said material phase delay to determine the instrument corrected material phase delay at those different frequencies, and determining a delta phase measurement from said corrected material phase delay at the different frequencies, and calculating the density or weight of said material from said delta phase measurements;

wherein said delta phase measurement is determined from the derivative of said instrument corrected material phase delays at the different frequencies and the determination of said delta phase measurement comprises:

unwrapping said instrument corrected material phase delay to provide a continuous curve of instrument corrected phase delay versus frequency, and determining therefrom the unwrapped instrument corrected phase delay, and determining the derivative from the unwrapped instrument corrected phase delay versus frequency to produce said delta phase measurement.

8. The process of claim 7 wherein said two or more primary microwave signals are generated sequentially.

9. The process of claim 7 wherein said material is selected from the group consisting cotton, hay, grain, tobacco, timber, lumber, and pulp.

10. The process of claim 7 wherein said material comprises a cotton bale.

11. The process of claim 7 wherein the determination of said delta phase measurement comprises:

unwrapping said instrument corrected material phase delay to provide a continuous curve of instrument corrected phase delay versus frequency, and determining therefrom the unwrapped instrument corrected phase delay, and calculating the difference between the highest and lowest frequency's unwrapped instrument corrected phase delay, and determining therefrom the derivative of the unwrapped instrument corrected phase delay versus frequency to produce said delta phase measurement.

* * * * *